US009897615B2

(12) United States Patent
Martens et al.

(10) Patent No.: US 9,897,615 B2
(45) Date of Patent: Feb. 20, 2018

(54) IMMUNOASSAY FOR FREE VITAMIN D

(75) Inventors: Michaël Franciscus Wilhelmus Cornelis Martens, Helmond (NL); George Henry Parsons, Arlington, MA (US); Franciscus Maria Anna Rosmalen, Wijchen (NL); Leon Maria Jacobus Wilhelmus Swinkels, Bemmel (NL)

(73) Assignee: Future Diagnostics, B.V., Wijchen (NL)

( * ) Notice: Subject to any disclaimer, the term of this patent is extended or adjusted under 35 U.S.C. 154(b) by 0 days.

(21) Appl. No.: 13/638,613

(22) PCT Filed: Apr. 1, 2011

(86) PCT No.: PCT/NL2011/050219
§ 371 (c)(1),
(2), (4) Date: Oct. 25, 2012

(87) PCT Pub. No.: WO2011/122948
PCT Pub. Date: Oct. 6, 2011

(65) Prior Publication Data
US 2013/0143241 A1     Jun. 6, 2013

(30) Foreign Application Priority Data
Apr. 1, 2010 (EP) ..................................... 10159035

(51) Int. Cl.
*G01N 33/82* (2006.01)

(52) U.S. Cl.
CPC ..................... *G01N 33/82* (2013.01)

(58) Field of Classification Search
None
See application file for complete search history.

(56) References Cited

U.S. PATENT DOCUMENTS

| 4,089,804 | A | * | 5/1978 | Falk | .................................. | 516/9 |
| 4,452,903 | A | * | 6/1984 | Lee et al. | ...................... | 436/540 |
| 5,981,779 | A | | 11/1999 | Holick et al. | | |
| 7,482,162 | B2 | * | 1/2009 | Laurie et al. | ................... | 436/20 |
| 2014/0147935 | A1 | * | 5/2014 | Imus Swinkels et al. | .... | 436/501 |
| 2017/0168077 | A1 | * | 6/2017 | Haddad | ............ | G01N 33/54366 |

FOREIGN PATENT DOCUMENTS

| WO | 03/023391 | 3/2003 |
| WO | 2008/039266 | 4/2008 |
| WO | 2008/092917 | 8/2008 |
| WO | WO 2008092917 A1 * | 8/2008 |

OTHER PUBLICATIONS

Jarvis et al., "Surface Chemistry of Fluorochemicals." U.S. Naval Research Laboratory, Surface Chemistry Branch Chemistry Division, (NRL Report 6324), (1965), p. 11-32.*
International Search Report for PCT/NL2011/050219, dated Jul. 14, 2011, (3 pages).
Hollis, B. W. et al, "Determination of Vitamin D Status by Radioimmunoassay with an 125I-Labeled Tracer", Clinical Chemistry, American Association for Clinical Chemistry, Washington, DC, vol. 39, No. 3, Jan. 1, 1993, pp. 529-533.

* cited by examiner

*Primary Examiner* — Ram R Shukla
*Assistant Examiner* — Ellen J Marcsisin
(74) *Attorney, Agent, or Firm* — Patterson Intellectual Property Law, PC; Seth R. Ogden; Emily A. Shouse

(57) ABSTRACT

Disclosed is the invention to conduct immuno-adsorption of free 25(OH) vitamin D from blood or blood components, notably serum or plasma, after which the absorbed material is measured. A fluoro-alkyl surfactant is used to enhance the solubility of Vitamin D and allow the measurement of free Vitamin D. The invention thus employs a binding protein to absorb the free 25(OH) vitamin D. Thereafter the binding protein comprising the 25-OH vitamin D is subjected to a competitive binding assay with a labeled vitamin D compound, preferably radiolabeled, fluorescent labeled, luminescent labeled, biotin labeled, gold labeled or enzyme labeled. Alternatively the immunocaptured 25-OH vitamin D can be quantitated by mass spectrometry.

7 Claims, 1 Drawing Sheet

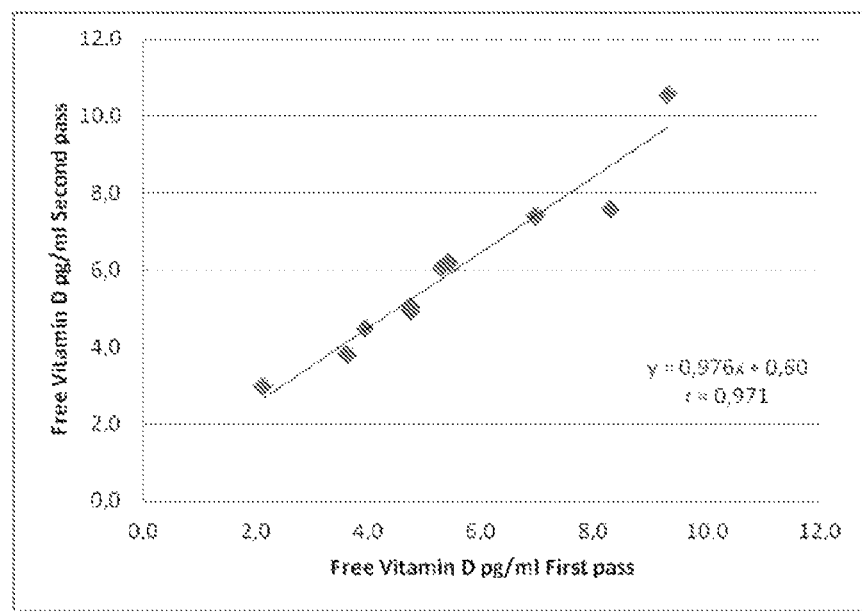

IMMUNOASSAY FOR FREE VITAMIN D

FIELD OF THE INVENTION

The invention relates to an immunoassay method for assaying a sample of blood or blood components for free vitamin D. The invention also relates to immunoassays and kits for conducting such immunoassays including point-of-care tests.

BACKGROUND OF THE INVENTION

The substances referred to as "vitamin D" encompass a group of fat-soluble prohormones, as well as metabolites and analogues thereof. The main forms in which vitamin D occurs in the body are vitamin $D_2$ (ergocalciferol) and vitamin $D_3$ (cholecalciferol). The latter is the endogenous form of vitamin D, which humans can form in the skin under the influence of sunlight. The former is an exogenous form of vitamin D, taken up with food. In the US, Vitamin D2 is used as the pharmaceutical vitamin D supplement. Unless indicated otherwise, the term Vitamin D in this disclosure refers to any form or forms of Vitamin D, including Vitamin D metabolites such as 25-hydroxy-Vitamin D or 1,25 dihydroxy Vitamin D.

Whilst vitamin $D_2$ and $D_3$ differ in the molecular structure of their side-chains, they share the same biological activity in being prohormones, metabolized in two steps to, ultimately, 1,25 dihydroxy vitamin D (1,25-(OH)-2-Vitamin D) also referred to as calcitriol, or 1,25 dihydroxy cholecalciferol). The preceding metabolite, 25-hydroxy vitamin D (25-(OH)-Vitamin D) or calcidiol, results from conversion in the liver, and is considered the storage form of vitamin D in the body.

Circulating vitamin D consists mainly of 25-(OH)-Vitamin D3 and 25-(OH)-Vitamin D2. Biologically, 25-(OH)-Vitamin D2 is as effective as 25-(OH)-Vitamin D3. The half-life of 25-(OH)-Vitamin D2 in the circulation is shorter. For clinical practice the use of a 25-(OH)-Vitamin D assay that measures both 25-(OH)-Vitamin D3 as well as 25-(OH)-Vitamin D2 is recommended (1).

Vitamin D has long been recognized as an important substance, the active form of which plays a role in the formation and maintenance of bone, as well as in other processes in the human or animal body. Thus, it serves to increase the flow of calcium into the bloodstream, by promoting absorption of calcium and phosphorus from food in the intestines, and re-absorption of calcium in the kidneys; enabling normal mineralization of bone and preventing hypocalcemic tetany. It is also necessary for bone growth and bone remodeling by osteoblasts and osteoclasts.

Vitamin D deficiency results in impaired bone mineralization and leads to bone softening diseases, rickets in children and osteomalacia in adults, and possibly contributes to osteoporosis.

Vitamin D plays a number of other roles in human health including inhibition of calcitonin release from the thyroid gland. Calcitonin acts directly on osteoclasts, resulting in inhibition of bone resorption and cartilage degradation. Vitamin D can also inhibit parathyroid hormone secretion from the parathyroid gland, modulate neuromuscular and immune function and reduce inflammation. Thus, it is of the essence for a person's or animal's health to have an adequate level of vitamin D.

Yet, excess of vitamin D (which may occur as a result of overdosing) is toxic. Some symptoms of vitamin D toxicity are hypercalcaemia (an elevated level of calcium in the blood) caused by increased intestinal calcium absorption. Vitamin D toxicity is known to be a cause of high blood pressure. Gastrointestinal symptoms of vitamin D toxicity can include anorexia, nausea, and vomiting. These symptoms are often followed by polyuria (excessive production of urine), polydipsia (increased thirst), weakness, nervousness, pruritus (itch), and eventually renal failure.

Clearly, it is important to be able to diagnose subjects for a possible vitamin D deficiency. It is also important, particularly for subjects that are on vitamin D supplementation, to be able to test subjects for a potential excess of vitamin D. The serum level of total 25-(OH)-Vitamin D is considered to be the primary indicator of the vitamin D status (2) However, this notion has been disputed.

Almost all circulating 25-(OH)-Vitamin D in serum is bound by Vitamin D Binding Protein (88%) and Albumin (12%). Vitamin D Binding Protein (DBP) is a major component of serum, with a concentration of 250-400 mg/L of serum. Only a small portion, about 2%, of the Vitamin D binding sites of DBP is occupied. A very small fraction, 0.04% of the 25-(OH)-Vitamin D, circulates in the free, non-protein bound form.

The concentration of DBP is not constant in all people and can be influenced by other factors including pregnancy, the use of oral contraceptives, renal disease and liver disease. Knowledge of the concentration of the DBP is crucial for accurate assessment of the patient's true 25-(OH)-Vitamin D status. For example, a young woman taking oral contraceptives could have a total 25-(OH)-Vitamin D level that was in the normal range. However, due to her elevated DBP, the concentration of Free 25-(OH)-Vitamin D could be markedly depressed, putting her at increased risk for clinical 25-(OH)-Vitamin D insufficiency and all the risks that that condition entails.

It has been shown that the physiological activity of thyroid and steroid hormones in vivo correlates better with their free, non-protein bound fraction, than with the total concentration of the hormone in plasma. Particularly in situations in which the level of binding proteins is elevated or decreased, the measurement of total circulating hormone may lead to a wrong diagnosis. In such situations the measurement of the concentration of the free circulating hormone provides better information. This notion is known as the "free hormone hypothesis". Mendel (3) suggested that the free hormone hypothesis is "likely to be valid with respect to all tissues for the thyroid hormones, for cortisol, and also for the hydroxylated metabolites of vitamin D.

Bikle et al (4) tested the validity of the free hormone hypothesis for 1,25-(OH)-2-Vitamin D. The data suggested that free 1,25-(OH)-2-Vitamin D levels appeared to be well maintained even in subjects with liver disease and reduced DBP levels, despite a significant decrease of the total 1,25-(OH)-2-Vitamin D.

In a subsequent study on 25-(OH)-Vitamin D the same group recommended to measure free 25-(OH)-Vitamin D in situations with modified concentrations of the binding protein. The author concluded that total vitamin D metabolite measurements may be misleading in the evaluation of the vitamin D status of patients with liver disease, and recommend that free 25-(OH)-Vitamin D levels also be determined before making a diagnosis of vitamin D deficiency. Bikle et al used ultrafiltration to determine the level of free 25-(OH)-Vitamin D (5). This method requires highly purified radio-labeled Vitamin D and tends to overestimate the fraction of free Vitamin D.

Lauridsen et al (6) showed that women with different DBP phenotypes have different concentrations of 1,25(OH)2VitD and 25(OH)VitD. These authors suggest that women with Gc2-2 are Vitamin D sufficient at lower plasma levels of 25(OH)VitD.

Some background art can be referred to regarding the determination of free analytes.

U.S. Pat. No. 4,366,143 describes an invention related to the assay of the free portion of organic substances or ligands that are present in biological fluids in a bound and a free form. The method essentially is a competitive immunoassay wherein, in one step, a labeled ligand, and a specific binder are added to a sample simultaneously. The free portion of the ligand and the labeled ligand compete for reaction with the specific binder, and become bound thereto in proportions which depend on the amount of the free ligand portion present in the sample. A drawback of the disclosed method is that, due to the presence of both the specific binder and the labeled ligand, a plurality of factors is present that are capable of disturbing the equilibrium between bound and free ligand, which makes the method less suitable for use with a free ligand that is present in a relatively low amount as is the case with Vitamin D. In fact, it is not disclosed how to use the assay for the measurement of free Vitamin D.

U.S. Pat. No. 4,292,296 discloses a method for the determination of free analytes in samples containing free analytes and receptor-bound analytes. The method involves two steps, the first being contacting a sample with an absorbent for the analyte to remove analyte from solution. The second step comprises contacting the absorbent-bound analyte with a labeled analyte analogue. Thereupon, the soluble phase is removed from the absorbent, and the amount of label in the bound and washed-away phases are determined. The method is described for determining the concentration of free thyroid hormones.

US patent application 2008/0182341 is related to stabilizing agents that are useful for the measurement of free or unbound analyte concentrations in a fluid. It is suggested that the stabilizers prevent dissociation of the ligand of its binding protein. The reference employs a simultaneous assay procedure, and lists a variety of stabilizing agents. The stabilizing agent is provided not to comprise an alkyl amine fluoro surfactant.

None of the prior art references specifically provides an assay for a determination of Vitamin D that reflects the status of free Vitamin D.

It is noted that assays for Free Vitamin D have been known for decades, but these use methods such as equilibrium dialysis or rate dialysis as their basis. Such methods are acceptable for researchers with highly trained technical staff, but are ill suited for routine laboratories who need high throughput automated tests to reach their financial goals. It is thus desired to provide an assay for free Vitamin D that is capable of being automated and which is suitable for use in point-of-care testing.

The foregoing numbered references are:
1. Hollis B W. Measuring 25-hydroxyvitamin D in a clinical environment: challenges and needs. Am J Clin Nutr. 2008 August; 88(2):507S-510S.
2. Holick M F. Vitamin D: extraskeletal health. Endocrinol Metab Clin North Am. 2010 June; 39(2):381-400.
3. Mendel C M. The free hormone hypothesis: a physiologically based mathematical model. Endocr Rev. 1989 August; 10(3):232-74.
4. Bikle D, Gee E, Halloran B, Haddad J. Free 1,25-Dihydroxyvitamin D Levels in Serum from Normal Subjects, Pregnant Subjects, and Subjects with Liver Disease. J Clin Invest. 1984; 74: 1966-1971.
5. Bikle D, Gee E, Halloran B, Kowalski M A, Ryzen E, Haddad J. Assessment of the free fraction of 25-hydroxyvitamin D in serum and its regulation by albumin and the vitamin D-binding protein. J Clin Endocrinol Metab. 1986 October; 63(4):954-9.
6. Lauridsen A L, Vestergaard P, Hermann A P, Brot C, Heickendorff L, Mosekilde L, Nexo E. Plasma concentrations of 25-hydroxy-vitamin D and 1,25-dihydroxy-vitamin D are related to the phenotype of Gc (vitamin D-binding protein): a cross-sectional study on 595 early postmenopausal women. Calcif Tissue Int. 2005 July; 77(1):15-22.
7. van Hoof H J, Swinkels L M, Ross H A, Sweep C G, Benraad T J. Determination of non-protein-bound plasma 1,25-dihydroxyvitamin D by symmetric (rate) dialysis. Anal Biochem 1998 May 1; 258(2):176-83.

SUMMARY OF THE INVENTION

In order to better address one or more of the foregoing desires the invention, in one aspect, presents a method for assaying a sample of blood or blood components for the presence of free Vitamin D (including Vitamin D metabolites such as 25-hydroxy-Vitamin D or 1,25 dihydroxy Vitamin D), comprising
(a) adding an immobilized binding protein or antibody for 25-OH vitamin D to the sample;
(b) mixing the sample with a diluent, said diluent comprising a fluoroalkyl surfactant;
(c) incubating the sample for an effective amount of time to allow a desired amount of 25-OH vitamin D to bind to the binding protein;
(d) removing the non-bound serum and serum components by washing;
(e) subjecting the immobilized binding protein or antibody comprising 25-OH vitamin D bound thereto, to competitive binding with a labeled vitamin D compound;
(f) determining the concentration of labeled vitamin D compound bound to the binding protein.

In another aspect, the invention resides in a kit for conducting the foregoing method.

In a further aspect, the invention pertains to a method for assaying a sample of blood or blood components for the presence of free Vitamin D, comprising in a first step capturing Vitamin D on an immobilized binder such as an immobilized binding protein or antibody for 25-OH vitamin D, and in a subsequent step the captured 25-OH Vitamin D is subjected to a competitive binding assay against a labeled vitamin D variant, wherein the capturing of free Vitamin D is effected by sequestering an amount of bound Vitamin D so limited as to satisfy a repetition test, wherein the sample from which the Vitamin D was captured is subjected to the same steps of capturing of Vitamin D and subjecting the captured Vitamin D to the same competitive binding assay, and wherein the measured concentration of free Vitamin D after both competitive binding assays is substantially the same.

In a still further aspect, the invention pertains to a method for assaying a sample of blood or blood components for the presence of free Vitamin D, comprising in a first step capturing Vitamin D on an immobilized binder such as an immobilized binding protein or antibody for 25-OH vitamin D, and in a subsequent step the captured 25-OH Vitamin D is subjected to a competitive binding assay against a labeled vitamin D variant, wherein the 0.5-5 wt. % of bound Vitamin D is captured.

In yet another aspect the method can be used for point-of-care" testing. The latter refers to testing at or near the site of patient care, i.e. rather than drawing blood samples and sending these to a diagnostic laboratory, a sample can be immediately introduced into a portable, preferably handheld device which is able to perform the assay in as limited a number of steps as possible, and with as limited a number of manual operations as possible.

In another aspect, the invention pertains to the use of a fluoroalkyl surfactant, preferably a perfluoro carboxylate surfactant, and more preferably perfluorooctanoic acid (PFOA), as a solubility enhancer for Vitamin D in an immunoassay for the determination of free Vitamin D.

DESCRIPTION OF DRAWING

FIG. 1 represents a correlation between free Vitamin D concentration in the first and the second pass of an assay of the invention. The line shown results from a repeated immunoextraction using 10 samples with different levels of free Vitamin D. The slope of the regression line is not significantly different from unity.

DETAILED DESCRIPTION OF THE INVENTION

In a broad sense, the invention concerns a two-step assay for the determination of free Vitamin D, comprising the immuno-adsorption of non-protein-bound 25(OH)-Vitamin D from blood or blood components, notably serum or plasma, after which the absorbed Vitamin D is measured.

Such samples can be drawn, in any manner known in the art, from a subject, particularly a human, in whose blood it is desired to assay the presence of free 25-OH-Vitamin D.

Free Vitamin D refers to the circulating, unbound fraction of Vitamin D. This relates to any form of Vitamin D, including Vitamin D2, Vitamin D3, and the metabolites 25(OH)-Vitamin D2, 25-(OH)-Vitamin D3, 1,25(OH)-2-Vitamin D2, and 1,25(OH)-2-Vitamin D3. The assay can be used to measure any of these forms of free Vitamin D, alone or in combination. Preferably, the assay of the invention is used to measure free 25(OH)-Vitamin D, resulting in the determination of 25(OH)-Vitamin D2 and 25-(OH)-Vitamin D3. The terms "free" and "unbound" refer to the fraction not bound to any protein, mainly including Vitamin D Binding Protein (VDBP or DBP).

The sample is preferably diluted before, during, or after the addition of the binding protein. The sample diluent can be aqueous-based, and preferably will be a buffer solution. Preferably, the buffered pH is in the range of from 6.0 to 8.0. The buffer includes a fluoro alkyl surfactant. It will be understood that mixing the buffer with the sample can be done by adding the diluent to the sample, by adding the sample to the diluent, or by simultaneously adding the buffer and the sample to each other. For practical reasons, it is preferred to add the diluent to the sample.

Without wishing to be bound by theory, the inventors believe that the surfactants enhances the solubility of Vitamin D in such a way as to result in a limited sequestering of Vitamin D.

In another aspect, the invention pertains to a novel concept for assaying free Vitamin D. A problem with assaying free Vitamin D is that the original concentration of free Vitamin D is very low and cannot be measured by existing immunoassays. Existing attempts to solve this problem are either based on the desire to avoid removal of Vitamin D from DBP (e.g. by attempts to "stabilize" the equilibrium between free and bound Vitamin D) or just involve surrendering to the fact that free DBP cannot be assayed, and these assays just involve displacement of Vitamin D from DBP.

In the invention, a limited sequestering of Vitamin D is foreseen, wherein the fraction of sequestered Vitamin D is low enough, preferably 0.1-10% of the total Vitamin D present in the sample, and preferably not exceeding 5% thereof, to still reflect the original free Vitamin D concentration.

This can be verified without undue experimentation in a simple by the addition of Tritiated Vitamin D and the dilution buffer. Vitamin D bound to the Vitamin D binding protein should not decrease by more than 5%. Alternatively, sample can be absorbed to the wall of antibody coated wells. After removing the sample, biotinylated Vitamin D is added and the free Vitamin D, absorbed to the antibody, is quantified. The sample from which an initial amount of Vitamin D is removed is introduced in a second well and again incubated and quantified. The measured concentration of free Vitamin D should be the same as the result from the first incubation.

Limited sequestering of Vitamin D is preferably achieved by the addition of 0.05 to 0.5% by weight of the fluoro alkyl surfactant, preferably 0.1-0.25%. Preferably the fluoro alkyl surfactant is a perfluoro alkyl surfactant, more preferably a perfluoro carboxylate surfactant, and most preferably perfluorooctanoic acid (PFOA). Preferably 0.1 to 0.2%, more preferably 0.15%, of PFOA is used. Under these conditions the response of samples with different levels of DBP, but the same concentration of total Vitamin D, was correlated with the concentration of free Vitamin D as measured by symmetric dialysis.

Conceivably, in the invention use can be made of PFOA itself, or a derivative thereof. These derivatives generally refer to derivatives comprising the perfluoro octanoic moiety, particularly including PFOA salts, such as PFOA ammonium salt, and to the corresponding sulfonic acid, viz. PFOA sulfonate, abbreviated as PFOS (perfluoro octane sulfonate, also known as perfluoro octane sulfonic acid).

An advantage of the method of determining Free Vitamin D (including Vitamin D metabolites) according to the invention is that it provides an assay format that is capable of being automated. This markedly distinguishes the assay of the invention from any pre-existing assay for the determination of free Vitamin D.

In the assay of the invention a binding protein for 25-OH-Vitamin D is added. Binding proteins, e.g. antibodies, for vitamin D are known in the art, and are widely used in the existing immunoassays for vitamin D. These same antibodies, as well as other binding proteins, can be used in the present invention as well. E.g., in the place of an antibody for Vitamin D an antibody fragment can be used such as produced with phage display technology. Suitable antibodies can be monoclonal or polyclonal antibodies. They can be obtained in known manner, e.g. polyclonal goat anti-vitamin D, polyclonal rabbit anti-vitamin D, or any other suitable antibody for vitamin D as known in the art from application in immunoassays for vitamin D. Suitable antibodies are known, e.g. from the following references: Hollis, Clin. Chem 31/11, 1815-1819 (1985); Hollis, Clin. Chem 39/3, 529-533 (1993).

The binding proteins are preferably added in a particulate form comprising solid carriers. Typically, the binding protein is coated on a solid phase, e.g. on a microtiter plate. In a preferred embodiment, the binding protein is coated onto magnetic particles, which facilitates their separation in a magnetic field.

After addition of the binding protein, e.g. an antibody, the sample is allowed to incubate. The required time will depend on circumstances such as the concentration of the reagents, the type of binding protein, and conditions during incubation, e.g. shaking and temperature. Generally, the incubation time will be in a range of from 10 seconds to several hours, preferably 1 minute to 2 hours. For automated platforms, short incubation times (10 seconds to 10 minutes, preferably 30 seconds to 30 minutes) are preferred. Basically, the period of time is not of particular relevance, as long as one determines in a calibration system how much of the free vitamin D is to be bound under the circumstances, during the desired period of time. Shorter and longer periods of time are expressly possible, provided that proper calibration takes place. Thus, preferably, comparison with calibrators involves the same period of time, under the same conditions After the incubation period, the sample can be subjected in a known manner to a competitive binding assay using a labeled vitamin D compound. Numerous labeled compounds are known that are capable of serving as competitive binding antigens in immunoassays for the determination of vitamin D. Typical labels are radiolabels, fluorescent labels, luminescent labels, biotin labels, gold labels, enzyme labels. Competitive binding assays are known to the skilled person, and do not require elucidation, notably since this part of the method of the invention can be carried out using any label known to be suitable for the determination of vitamin D. Labels that can be used are, inter alia, those disclosed in the foregoing references on existing vitamin D immunoassays.

With the label allowing measuring a concentration, as a result, the concentration of free vitamin D in the sample is determined. It will be understood that the interpretation of the values measured, is determined by a calibration measurement, i.e. by the response—in the same assay—of calibrators.

Alternatively, the captured Vitamin D can be subjected to quantitative analysis by means of mass spectroscopy.

The calibration for the assay of the invention can be done by providing calibrators comprising a predetermined concentration of free 25-OH-Vitamin D. The fraction of free Vitamin D in these calibrators may be determined by symmetric dialysis. In symmetric dialysis a serum sample is loaded on one side of a dialysis cell. The other compartment is loaded with the same sample in which a trace amount of radiolabeled Vitamin D is added. The rate of migration of the radiolabeled Vitamin D from one dialysis compartment to another is directly proportional to the free fraction of Vitamin D (7).

The measurement of free vitamin D according to the invention relies on the assessment of the concentration of free Vitamin D without substantially affecting the concentration of free Vitamin.D, yet on the basis of a limited sequestering of Vitamin D as discussed above.

The invention, in another aspect, presents a product in the form of an immunoassay for the determination of 25-OH vitamin D in blood or blood components, wherein the assay makes use of a method according to any one of the preceding embodiments. More particularly, such a product will be provided in the form of a kit for conducting the immunoassay. Such a kit may comprise the individual reagents involved, i.e. the binding protein and the labeled vitamin D compound. These reagents can be provided separately, and thus form a kit only upon their use in the assay of the invention. Preferably, the reagents are provided together, preferably packaged together, as one kit of parts. The kit optionally comprises a container for a sample of blood or blood components, but as is customary this may also be provided separately. Typically a kit comprises a binder immobilized on a solid phase and a separate conjugated vitamin D. Other kit components will depend, as is customary in the art, on the label chosen, as different labels may require different reagents.

The invention also pertains to the use of a fluoroalkyl surfactant, a perfluoro carboxylate surfactant, and more preferably perfluorooctanoic acid and/or perfluoroheptanoic acid, as a solubility enhance for Vitamin D in an immunoassay for the determination of free Vitamin D.

Preferred surfactants perfluoro alkyl surfactants, more preferably perfluoro carboxylates such as perfluoroheptanoic acid or perfluorooctanoic acid. Most preferably, the surfactant is perfluorooctanoic acid (PFOA), or a derivative thereof. These derivatives generally refer to derivatives comprising the perfluorooctanoic moiety, particularly including PFOA salts, such as PFOA ammonium salt, and to the corresponding sulfonic acid, viz. PFOA sulfonate, abbreviated as PFOS (perfluoro octane sulfonate, also known as perfluoro octane sulfonic acid). The analogous derivatives of other perfluoro carboxylate surfactants can also be used.

It is to be understood that the invention is not limited to the embodiments and formulae as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

The invention will be illustrated with reference to the following, non-limiting Example and the accompanying non-limiting FIGURE.

EXAMPLE

Materials

Coated Microtiterplates
Nunc maxisorp micotiterplates were coated with an anti-mouse IgG antibody at a concentration of 200 ng/well. Subsequently a layer of monoclonal anti-25(OH) vitamin D antibody was absorbed onto the anti-mouse IgG layer at a concentration of 2 ng/well. The plates were blocked with a borate buffer containing BSA and sucrose.
The Sample Diluent
The sample diluent consists of a 0.1M TRIS buffer of pH 8.0 containing preservatives and 0.15% of PFOA.
The Conjugate
(i.e. the labeled vitamin D compound) is a biotinylated Vitamin-D. The conjugate was presented at a concentration of 25 pg/ml in 0.1M Tris buffer of pH 7.5 containing 0.1% Bovine serum albumin and preservatives.
Streptavidin-HRP and TMB were from a commercial source.
Protocol
The assay is performed as follows. In the well of a micotiterplate, 90 µl of sample diluent is pipetted. Next, 10 µl of sample is added to the diluent. This mixture is incubated for 90 minutes at 37° C. Subsequently, the wells are washed three times with washbuffer. 100 µl of HRPConjugate is added to the cuvette and incubated for 30 minutes. Again the wells are washed three times with washbuffer. A colorimetric signal is then generated by addition of Horse Radish Peroxidase labeled streptavidin. After 20 minutes incubation at 37° C. the wells are washed three times with washbuffer. Subsequently 100 µl of TMB solution is added to the wells.

After a 20 minutes incubation at room temperature in the dark 100 μl of stop solution is added and the absorbance is read at 450 nm.

The signal generated in the well is inversely proportional to the concentration of free 25 (OH)Vitamin D in the sample or calibrator. The concentration of free 25(OH) vitamin D in the original sample can be calculated by comparing the signal of unknowns with the response of calibrators.

Results

Using the assay of the invention on standard reference samples, a typical calibration curve for the measurement of free 25(OH) Vitamin D is generated and illustrated in the table below.

| | Calibrators | | | | |
|---|---|---|---|---|---|
| | Calibrator A | Calibrator B | Calibrator C | Calibrator D | Calibrator E |
| Free 25(OH)D3 [pg/ml] | 1.1 pg/ml | 4.2 pg/ml | 8.6 pg/ml | 16.2 pg/ml | 41.6 pg/ml |
| Abs. 450 nm | 2.304 | 1.856 | 1.177 | 0.514 | 0.132 |
| Abs. 450 nm | 2.291 | 1.808 | 1.151 | 0.517 | 0.123 |
| Average OD | 2.298 | 1.832 | 1.164 | 0.516 | 0.128 |
| CV % | 0.40% | 1.85% | 1.58% | 0.41% | 4.99% |
| Binding percentage % | 100% | 80% | 51% | 22% | 6% |

Samples of blood or blood components of human or animal subjects, e.g. of patients, can be subjected to the assay of the invention. The measured amounts of Vitamin D can be correlated with the calibration curve, and thus interpreted.

The invention claimed is:

1. A method for assaying a sample of blood or blood components for the presence of circulating, unbound vitamin D, comprising;
   (a) adding an immobilized antibody for 25-OH vitamin D to the sample;
   (b) mixing the sample with a diluent, said diluent comprising a fluoroalkyl surfactant wherein the fluoroalkyl surfactant is present at a level of 0.1-0.2% by weight and the fluoroalkyl surfactant is a perfluorooctanoic acid;
   (c) incubating the sample for an effective amount of time to allow a desired amount of circulating, unbound Vitamin D to bind the antibody for 25-OH vitamin D;
   (d) removing the non-bound sample components by washing;
   (e) subjecting the immobilized antibody comprising captured vitamin D bound thereto, to competitive binding with a labeled vitamin D compound;
   (f) determining the concentration of labeled vitamin D compound bound to the immobilized antibody, whereby the concentration of labeled vitamin D compound is a measure for the concentration of circulating, unbound vitamin D, the concentration being determined with reference to a calibrator concentration for vitamin D,
   wherein the perfluorooctanoic acid does not dissociate vitamin D from Vitamin D Binding Protein and albumin.

2. The method of claim 1, wherein said diluent has a buffered pH in the range of 6.0 to 8.0.

3. The method of claim 1, wherein the sample is human serum or plasma.

4. The method of claim 1, wherein the antibody for 25-OH vitamin D is provided in a form coated on magnetic particles.

5. The method of claim 1, wherein the labeled vitamin D compound comprises a label selected from the group consisting of radiolabels, fluorescent labels, luminescent labels, biotin labels, gold labels and enzyme labels.

6. The method of claim 1, wherein the circulating, unbound vitamin D is a vitamin D metabolite.

7. The method of claim 6, wherein the vitamin D metabolite is 25-hydroxy-Vitamin D or 1,25 dihydroxy Vitamin D.

* * * * *